United States Patent [19]
Sturgill

[11] Patent Number: 5,107,841
[45] Date of Patent: Apr. 28, 1992

[54] MAXIMUM ENTROPY VELOCITY ESTIMATOR FOR ULTRASONIC FLOW IMAGING SYSTEM

[75] Inventor: Michael R. Sturgill, Phoenix, Ariz.

[73] Assignee: Acoustic Imaging Technologies Corporation, Tempe, Ariz.

[21] Appl. No.: 525,090

[22] Filed: May 16, 1990

Related U.S. Application Data

[63] Continuation-in-part of Ser. No. 441,787, Nov. 27, 1989, abandoned.

[51] Int. Cl.$^5$ .............................................. A61B 8/06
[52] U.S. Cl. ............................ 128/661.09; 73/861.25
[58] Field of Search .................. 128/661.08–661.09; 73/861.25

[56] References Cited

U.S. PATENT DOCUMENTS

| | | | |
|---|---|---|---|
| 4,719,923 | 1/1988 | Hartwell et al. | 128/661.08 |
| 4,759,374 | 7/1988 | Kierney et al. | 128/661.08 |
| 4,770,184 | 9/1988 | Greane, Jr. et al. | 128/661.08 |

*Primary Examiner*—Francis Jaworski
*Attorney, Agent, or Firm*—Christie, Parker & Hale

[57] ABSTRACT

A system for improving the flow estimation sensitivity of an ultrasonic Doppler flow imaging system includes an ultrasonic wave tranmitter and receiver for sequentially transmitting ultrasonic waves toward and into a living body and for receiving the reflected Doppler-shifted echo signals. A series of echo signals received from each of a number of points within the body are processed in a velocity estimator, using maximum entropy techniques, to produce an output signal representative of an estimated velocity of the flow at each of said points within the body. The processing means detects the series of echo signals for each point and calculates an average power spectrum based on the amplitude-versus-frequency distribution of the series of received echo signals. The power spectrum is calculated by fitting a first order polynomial to the series of echo signals, although higher order polynomials can be used. A peak center frequency shift associated with the data detected for each point is derived from the power spectrum. The resulting peak center frequency shift information is then processed to produce a velocity estimate for each of the points at which velocity is being measured, and the resulting velocity estimate information is then processed further for imaging in a two-dimensional Doppler color flow imaging display.

21 Claims, 5 Drawing Sheets

MAXIMUM ENTROPY VELOCITY ESTIMATOR FOR ULTRASONIC FLOW IMAGING SYSTEM

CROSS-REFERENCE

This is a continuation-in-part of application Ser. No. 07/441,787, filed Nov. 27, 1989 and now abandoned.

FIELD OF THE INVENTION

This invention relates to ultrasonic diagnosis techniques, and more particularly to ultrasonic Doppler blood flow imaging and display systems. The invention is particularly directed to techniques for improving the flow estimation sensitivity of an ultrasonic color flow imaging system.

BACKGROUND OF THE INVENTION

Various techniques have been used in the past to achieve noninvasive imaging of blood flow using ultrasound. Recent developments in Doppler echocardiography are an example.

A typical ultrasound blood flow imaging system includes an ultrasonic transmit-receive transducer for transmitting ultrasonic pulses into a region of the body under diagnosis and for receiving echo signals of the transmitted ultrasound waves reflected due to blood flow in the area being scanned. A typical diagnosis with ultrasound includes scanning the patient with the ultrasound probe to measure blood flow in an artery, a vein, or in the heart. A signal processing system processes the received echo signals for measuring the Doppler shift frequency of the echo signals for use in calculating the velocity of the blood flow, and the result of the velocity distribution measurement is displayed as a Doppler blood flow image.

In order to estimate the Doppler shifts of the echoes received from the blood cells, an ultrasound imaging system commonly transmits pulses at one location in the region under diagnosis and then detects the variations in the phase of the echoes from pulse to pulse.

Echo signal components Doppler shifted by the blood flow are extracted from the Doppler signal components carrying the information of the internal moving part of the body. Typically, an MTI (moving target indication) filter (also referred to as a stationary canceller) is used to eliminate "clutter" signals reflected from stationary or slowly moving targets such as the wall of the heart or blood vessels, and only the signal components Doppler-shifted by the blood flow being measured are extracted. The MTI filter output is then typically processed in a velocity estimator to extract the Doppler frequency information which is converted to velocity data displayed in color to provide a two-dimensional image of the blood flow being measured.

The present invention is concerned with improving the flow estimation sensitivity of a Doppler color flow imaging system. The techniques provided by this invention are based on maximum entropy spectral estimation. Unlike classical power spectrum estimation techniques, this method does not suffer from the inherent "windowing" problems present in all finite-length sampled data sequences. The present method allows higher speed imaging resulting from needing fewer data samples to estimate velocity accurately. The method also provides improved velocity detection sensitivity in signals highly contaminated by noise. The invention offers reduced sensitivity to quadrature phase errors, resulting in relaxed constraints on the analog demodulator used in the system for input to the velocity estimator. The number of multiply and accumulate operations increases linearly with sequence length, as opposed to some Discrete Fourier Transform techniques which increase at an $N^2$ rate, and this has additional advantages.

SUMMARY OF THE INVENTION

Briefly, one embodiment of this invention provides a system for improving the flow estimation sensitivity of an ultrasonic Doppler flow imaging system which includes ultrasonic wave transmitting and receiving means for sequentially transmitting ultrasonic waves toward and into a living body and for receiving the reflected Doppler-shifted echo signals. The system includes means for processing a series of echo signals received from each of a number of points within the body for producing an output signal representative of an estimated flow velocity at each of those points. The processing means detects the series of echo signals for each point and calculates an associated power spectrum based on the amplitude-versus-frequency distribution of the series of echo signals. In one embodiment, the power spectrum is derived by means for fitting a first order polynomial to the series of echo signals, and a peak center frequency shift is calculated based on the resulting power spectrum. The center frequency shift data are then processed for producing an output representative of a velocity estimate for each of the points where velocity is measured. In other embodiments, higher order polynomials can be used in calculating a related power spectrum estimation. Estimated velocity information is displayed as a two-dimensional color image of the flow being measured. BRIEF DESCRIPTION OF THE DRAWINGS FIG. 1 is a functional block diagram illustrating a blood flow measuring and imaging system which includes a color velocity estimator according to principles of this invention;

DETAILED DESCRIPTION

Figure 1:
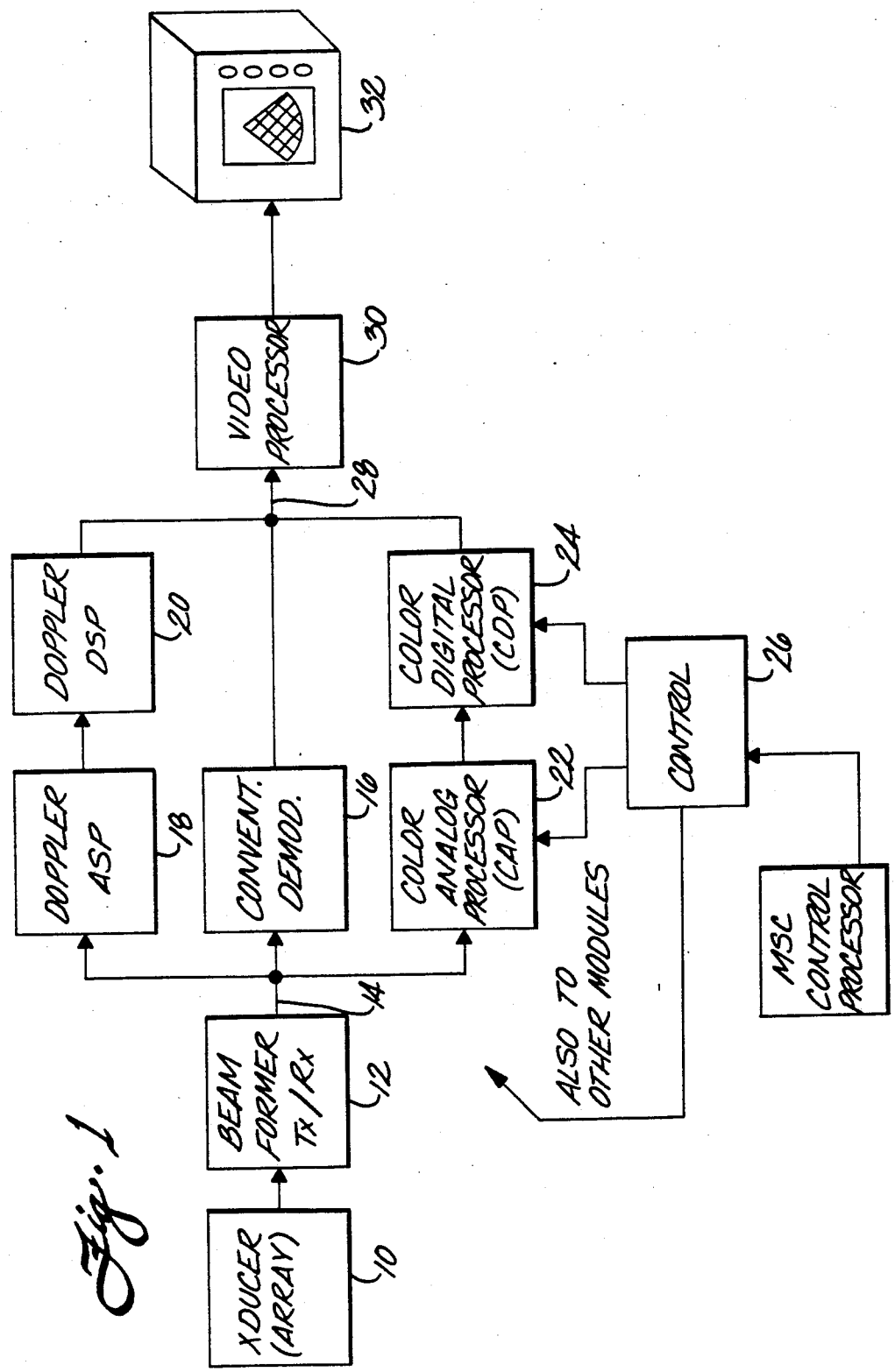

FIG. 1 is a functional block diagram illustrating components of a blood flow measuring and imaging system which generally includes a transmit-receive transducer 10 and a beamformer 12 for producing an ultrasonic pulse beam 14 which can be directed toward a blood vessel in a sector of a living body under examination. The transducer typically includes an array of elements, each of which transmits and receives separate pulse beams directed to a particular location under diagnosis. One example of the use of the invention is to measure blood flow in an artery of the heart.

The ultrasonic pulse beams reflected due to the blood flow being measured are then sent to a signal processing system for further processing to measure velocity of the blood flow at the location under analysis. The FIG. 1 block diagram illustrates three parallel techniques, any of which may be selected, for processing the ultrasonic pulse beams 14. One technique is by conventional demodulation detection techniques 16, a second technique uses a Doppler analog signal processor 18 and a Doppler digital signal processor 20, and a third technique provided by this invention includes a color analog processor 22 and a color digital processor 24. Within the color digital processor are a number of algorithms, including the velocity estimator algorithm used according to this invention. The control function shown at 26 in the block diagram of FIG. 1 includes a real-time controller and transient timing. All output signals 28 from either the conventional, Doppler, or color processing loops are in the same form and are input to a video processor 30 which includes a scan converter. Velocity information is observed from color imaging displayed on a TV monitor 32.

Figure 2:
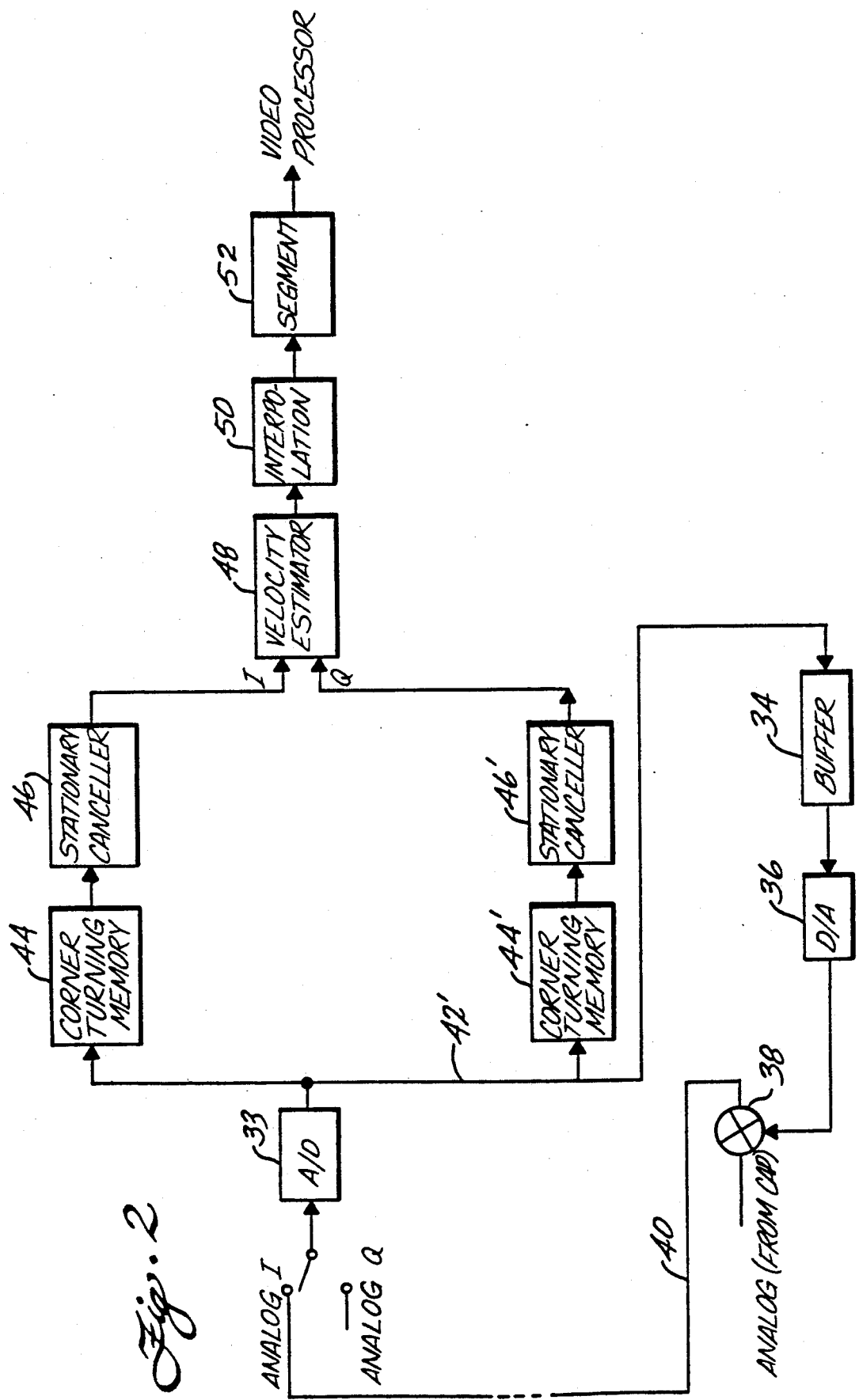
FIG. 2 is a functional block diagram illustrating components of a color digital processor shown in FIG. 1.

FIG. 2 illustrates digital processing in the color digital processor 24 generally illustrating the techniques for making the velocity estimate. The beamformer output 14 (see FIG. 1) is demodulated in the color analog processor 22 and its analog output is then sent to the color digital processor 24. Multiple ultrasonic pulse beams are transmitted into the body at each of a number of locations in an area under diagnosis, and for each location, a plurality of reflected echo signals are received during successive predetermined time intervals. Each received echo signal normally has a stationary component reflected from essentially stationary tissue and a Doppler component reflected from areas where movement is sensed, such as blood flow. The reflected echo signals are processed in a canceller having stationary signal acquisition and Doppler signal acquisition modes, in that order, for each flow measuring sequence. In the stationary acquisition mode, an ultrasound basis line is first transmitted, and its echo is detected, converted to digital in an analog-to-digital converter 33 and then stored in a line buffer 34 shown in FIG. 2. The system then switches to the Doppler acquisition mode, and on each of the succeeding pulses the stored line samples are recalled from the line buffer 34, converted to analog form in a digital-to-analog converter 36, and subtracted from the succeeding reflected echo signals at a summing junction 38. The difference or residue 40 is amplified to boost the gain of the signal, and this signal is then converted to digital in the analog-to-digital converter 33. The resulting digital signals 42 representing the distribution of Doppler sound pulses over time are then processed further to estimate blood flow velocity.

Figure 3:
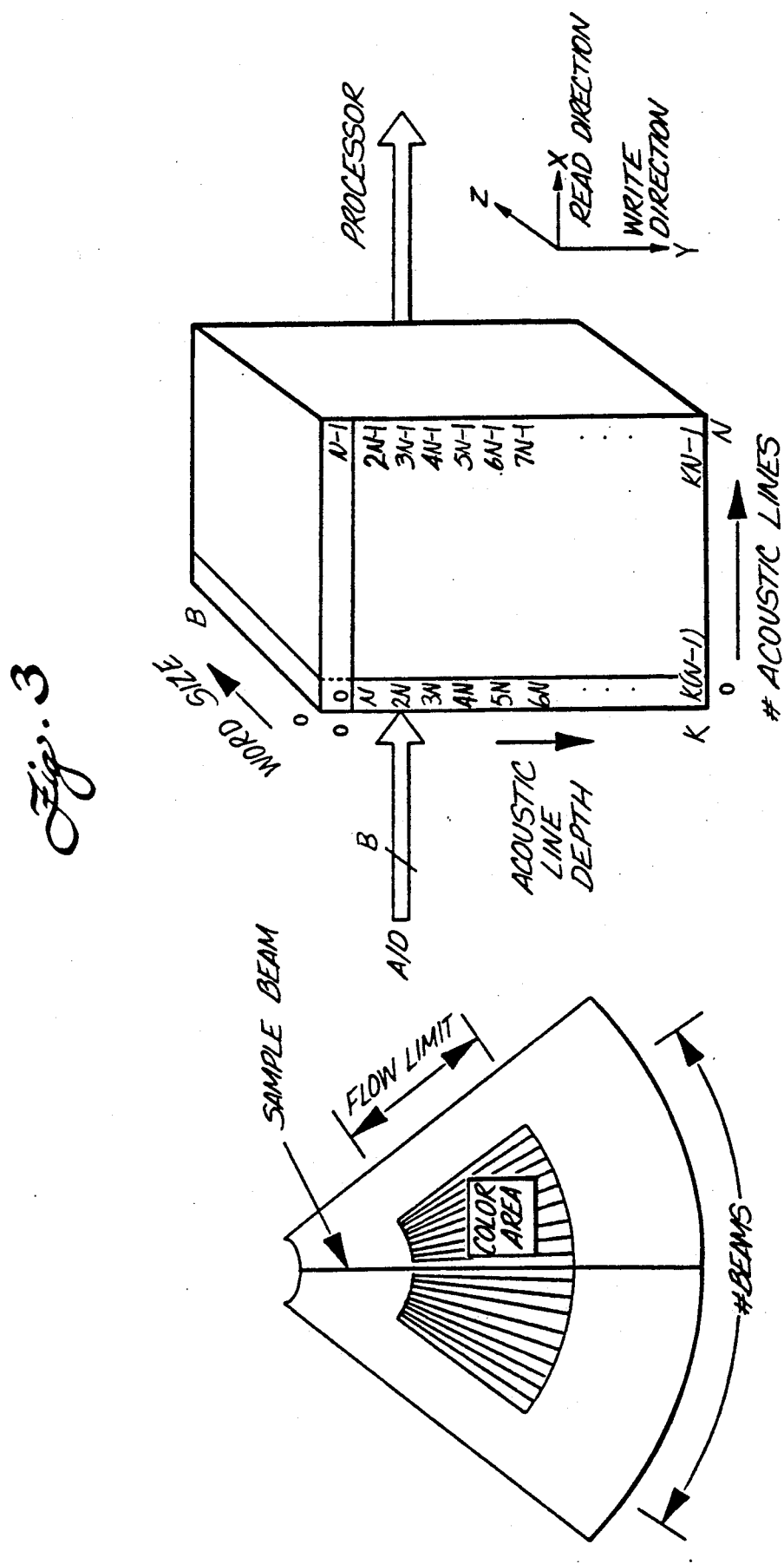
FIG. 3 is a schematic diagram illustrating operation of a corner-turning memory used in the system shown in FIG. 2.

The I and Q components of the digital signals 42 from the analog-to-digital converter 33 are each sent to a separate corner-turning memory 44 schematically illustrated in FIG. 3. In the illustrated embodiment, the corner-turning memory comprises a color two-dimensional scan and corner-turning random access memory having K rows by N columns by B bits deep in which vertical is the write direction and horizontal is the read direction. Data from each scan line are written into a separate column of the memory and data for a scan line at a later time interval are written into a second column, and so forth. Data read from any given row N give the data samples for a given point in space.

The acoustic line data read from the corner-turning memory 44 are sent to a stationary canceller 46 for further removal of DC components representing signals from stationary or slow moving targets.

The I and Q components of the data signals are then sent to a velocity estimator 48 using maximum entropy techniques (described below) of this invention for determining a velocity estimate at each point in space at which velocity is being measured. The maximum entropy techniques are used to measure frequency shift by calculating the average or center frequency shift from the data available from each point toward which a scan line is directed. The frequency shift data are then processed by an interpolation network 50 which calculates a peak frequency component. For instance, frequency data may be available in the form of several peak amplitudes spaced apart along the frequency axis. The maximum average peak frequency can occur at a peak line between two of the highest peak frequencies shown in the input data. Interpolation techniques calculate a single peak frequency located between the two peak frequency data points that provides a best estimate of the maximum average peak frequency value. The data from the interpolator are then sent to a segmentation processor 52 to determine whether the estimate is valid. The output from the segmentation processor is sent to the video processor 30 to produce a color flow image on the TV screen 32.

The maximum entropy techniques will now be described. As mentioned previously, in order to estimate blood flow velocities, a number of pulses must be transmitted into the tissue. When these transmitted ultrasonic waves contact blood cells which are moving, the frequency of the transmitted pulse is shifted. The direction of the frequency shift and the amount of shift are a function of the flow velocity. This shift is referred to as the Doppler frequency shift.

The accuracy of the measurement of the velocity estimate is directly proportional to the accuracy of the measured Doppler frequency shift. The velocity of blood flow is related to the Doppler frequency through the Doppler equation given in Eq. (1):

$$\bar{v} = \frac{\bar{\omega} \cdot c}{\omega_o \cdot 2\cos(\theta)} \quad (1)$$

where
$\bar{v}$ is the estimated blood velocity
$\bar{\omega}$ is the measured Doppler frequency shift
$\omega_o$ is the transmitted probe frequency
c is the speed of ultrasound in the body
$\theta$ is the angle of the interrogating ultrasound wavefront relative to the direction of blood flow.

The maximum entropy method (MEM) of spectral analysis has been used in seismic, radar, and sonar applications. These applications use greater than first order estimates and have much larger sequence lengths than contemplated for this invention. The method's complexity has limited its utility in high speed real-time systems. Maximum entropy spectral analysis has superior frequency resolving capabilities compared with classical spectral estimation techniques.

The measurement of blood velocities is complicated by many factors. One major difficulty is in measuring a Doppler frequency shift from very few data points (perhaps 4-16) which are highly contaminated by noise. Under these constraints, velocity estimation based on classical techniques such as Discrete Fourier Transform (DFT), Fast Fourier Transform (FFT), and Correlation produce results whose accuracies are limited by the window functions which they use. Even if no window function is explicitly used on the data, the finite data lengths introduce a boxcar window function.

The estimation of a power spectrum from a time series autocorrelation function, $R(t), |t| \leq N$, has been shown to be the Fourier transform of the autocorrelation function. The normal assumption about this autocorrelation function is that its values are zero outside the interval of known values, i.e., $|t| > N$. This approach places a rectangular window around the autocorrelation function. Thus, by Fourier transforming this windowed function, the resultant estimated spectrum is the convolution of the Fourier transforms of the true spectrum and the window function. The selection of a suitable window function involves the compromise between frequency resolution and the contamination of one spectral component by another.

Maximum entropy spectrum analysis is based upon choosing the spectrum which corresponds to the most random or the most unpredictable time series whose autocorrelation function agrees with the known values. This assumption has been shown to be maximally non-committal with regard to the unknown values of the autocorrelation function. In other words, instead of selecting $R(t)=0$ for $|t|>N$, these autocorrelation values are chosen to maximize the entropy per sample of the time series.

The maximum entropy principle for estimating the power spectrum of a complex time series can be stated as follows:

Find the power spectrum, $P(f)$, that maximizes the value of $$\int_{-W}^{W} \ln(P(f)) df \quad (2)$$

under the constraint that $P(f)$ satisfies a set of N functional measurement equations $$g_n = \int_{-W}^{W} P(f) G_n(f) df \; n = 0, 1, \ldots, N. \quad (3)$$

It is assumed that the time series is sampled at a uniform period of $\Delta t$ where $W=1/(2\Delta t)=$ the Nyquist frequency and that the power spectrum of the time series is band limited to $\pm W$. The $G_n(f)$ are the test functions and the $g_n$ are the resulting values of the measurements.

For a given power spectrum, the entropy is proportional to the integral of the logarithm of the spectrum. Therefore, the maximum entropy time series is the time series whose spectrum maximizes Eq. (2) under the constraint of Eq. (3).

The PSD (Power Spectral Density) of the input data is found by evaluating an all pole filter as a function of frequency whose coefficients are found using the MEM. The equation for the PSD is given in Eq. (4)

$$P(f) = \frac{P_{M+1}}{\left|1 - \sum_{k=1}^{M} \alpha_{M,k} \exp(-j2\pi f k \Delta t)\right|^2} \sum_{i=-M}^{M} \phi_i \exp(-j2\pi f i \Delta t) \quad (4)$$

where $P_{M+1}$ and $\alpha_{M,k}$ are the coefficients to be found. Eq. (4) implies a linear set of relations between the autocorrelations $\phi_i$ and the coefficients $\alpha_{M,k}$. They satisfy the matrix equation of (5).

$$\begin{bmatrix} \phi_0 & \phi_1 & \phi_2 & \ldots & \phi_M \\ \phi_1 & \phi_0 & \phi_1 & \ldots & \phi_{M-1} \\ \phi_2 & \phi_1 & \phi_0 & \ldots & \phi_{M-2} \\ \vdots & & & & \vdots \\ \phi_M & \phi_{M-1} & \phi_{M-2} & \ldots & \phi_0 \end{bmatrix} \begin{bmatrix} 1 \\ \alpha_1 \\ \alpha_2 \\ \vdots \\ \alpha_R \end{bmatrix} = \begin{bmatrix} P_{M+1} \\ 0 \\ 0 \\ \vdots \\ 0 \end{bmatrix} \quad (5)$$

The matrix of Eq. (5) is a symmetric Toeplitz matrix where the $\phi_i$ and $\alpha_{Mk}$ are in general complex. The Toeplitz matrix is of order $[M \times M]$ and the maximum entropy method gives an estimate of the autocorrelation value $\phi_{M+1}$. An efficient algorithm for the calculation of the unknown coefficients was originated by Burg and is presented here.

Initially, dummy parameters $b_{Mk}, b'_{Mk}; k=1, 2, \ldots, N-M$, where N is the input data record length, are calculated as follows.

$$b_{Mk} = b_{M-1,k} - \alpha^*_{M-1,M-1} \cdot b'_{M-1,k} \quad (6)$$

$$b'_{Mk} = b'_{M-1,k+1} - \alpha_{M-1,M-1} \cdot B_{M-1,k+1} \quad (7)$$

where $b_{M-1,k}, b'_{M-1,k}$ are previously defined values. Now the $\alpha_{Mk}$ are calculated as follows.

$$\alpha_{MM} = \frac{2 \sum_{k=1}^{N-M} b_{Mk}^* b'_{Mk}}{\sum_{i=1}^{N-M} (|b_{Mk}|^2 + |b'_{Mk}|^2)} \quad (8)$$

$$\alpha_{Mk} = \alpha_{M-1,k} - \alpha_{MM} \cdot \alpha^*_{M-1,M-k} \; 1 \leq k \leq M-1 \quad (9)$$

and $$P_{M+1} = P_M \cdot (1 - |\alpha_{MM}|^2) \quad (10)$$

The initial values are $$b_{1k} = x_k \; k = 1, 2, \ldots, N-1 \quad (11)$$

$$b'_{1k} = x_{k+1} \; k = 1, 2, \ldots, N-1$$

$$\alpha_{MO} = -1$$

$$\alpha_{MK} = 0, k > M$$

and $$P_0 = \sum_{k=1}^{N} |x_k|^2 / N$$

Equations (6) and (7) are not used for $M=1$.

Equation (4) shows the power spectral density relationship of the coefficients $\alpha_{Mk}$. Equation (4) is a polynomial in z where $z=e^{j\omega t}$. By expanding the denominator of (4) inside the $||^2$ brackets, the following results:

$$1 - \sum_{k=1}^{M} \alpha_{Mk} z^{-k} = 1 - \alpha_1 z^{-1} - \alpha_2 z^{-2} - \ldots - \alpha_M z^{-M} \quad (12)$$

where M is the length of the prediction error filter and N is the length of the input data record, $M < N$.

This type (autoregressive) of spectral analysis is based on the idea that, if it is possible to design a feed forward (all zero) filter whose input is the data to be analyzed, and whose output is white noise, then the power spectrum of the input data is given by the reciprocal of the power transfer function of the filter. The filter accounts for all the predictability inherent in the input signal and has at its output only unpredictable white noise. This filter is referred to as a prediction-error filter (PEF).

The maximum entropy method derives these PEF coefficients directly from the data and does not make any unnecessary assumptions about the unknown data.

One parameter which can be varied is the order of the estimation. This order corresponds to the number of poles in the prediction error filter. Since some a priori knowledge of the ultrasound signal can be assumed, namely, a sinusoid with some bandwidth and additive noise, a first order estimate is used. The first order estimate has some very desirable properties for this estimate. The first is that only one peak occurs in the power spectrum, making the peak detection algorithm easier. This peak occurs at the average frequency contained in the input sequence. A number of algorithmic simplifications can be made when using a first order estimate including lessening the computational burden. Once the coefficient of the PEF has been determined, any number of frequency components may be determined since the power spectrum is fully characterized at this point.

Figure 4:
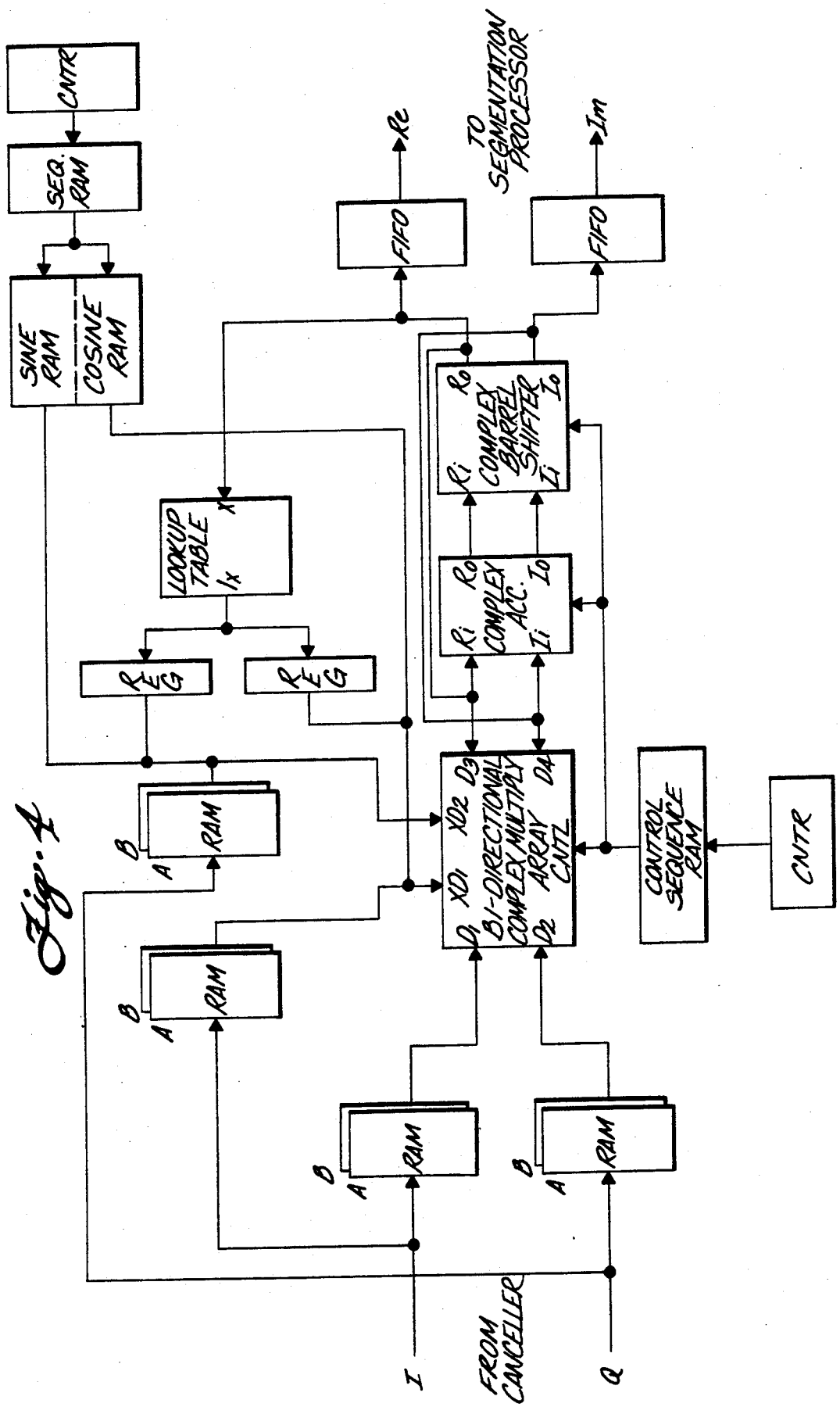
FIG. 4 is a schematic functional block diagram illustrating a maximum entropy velocity estimator according to principles of this invention.

FIG. 4 illustrates a maximum entropy velocity estimator functional block diagram for calculating the center frequency shift used to determine the flow velocity estimate for each point at which velocity is measured.

Figure 5:
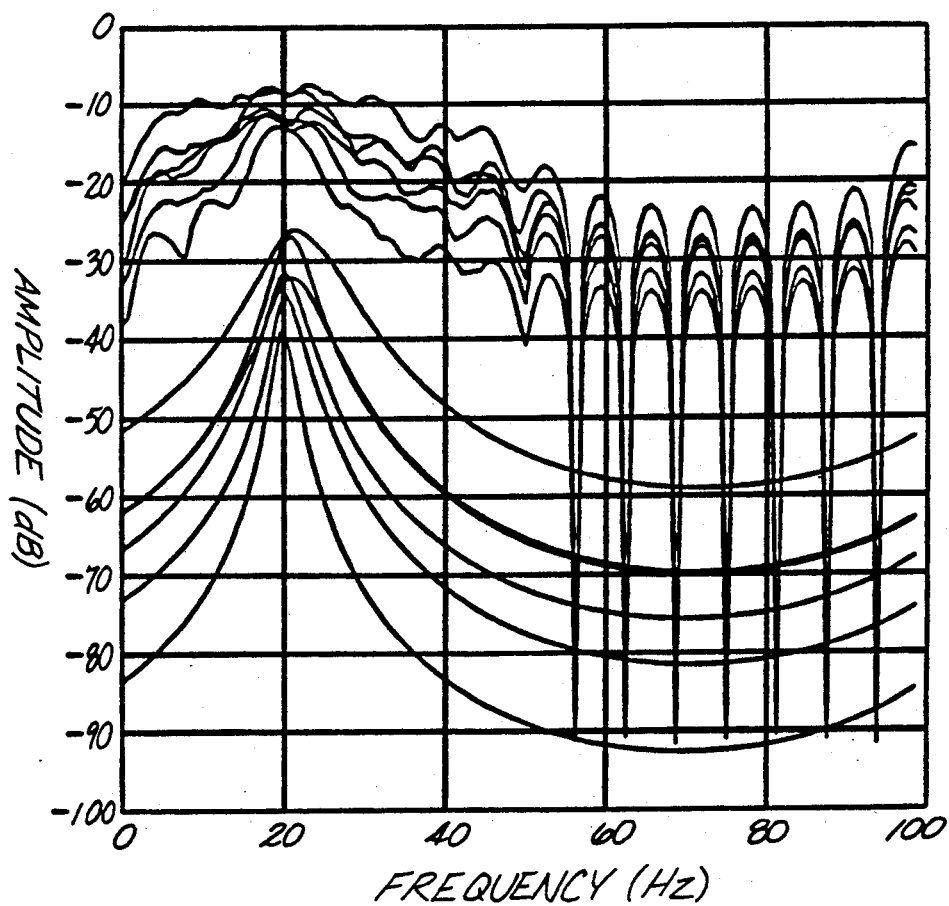
FIG. 5 is a graph showing a spectral comparison between Discrete Fourier Transform techniques and the maximum entropy techniques of this invention for identical input data.

FIG. 5 shows a comparison between the Discrete Fourier Transform and the Maximum Entropy Method. The family of plots was formed by generating quadrature sinusoid with bandwidths ranging from 2 to 20 hertz. The lower family of plots are the maximum entropy method and the upper plots are the DFT. The tone's center frequency was 20 Hz in all cases. These frequencies are normalized and can be scaled to indicate a center frequency of 2000 Hz with bandwidths ranging from 200 to 2000 hertz. It is easily seen how much more distinct the frequencies appear with MEM.

It can also be seen how the bandwidths of the individual tones spread symmetrically around the peak. This allows the spectral variance to be readily measured. Spectral variance is a measure of the blood's turbulence which is another important diagnostic measure.

What is claimed is:

1. A system for improving the flow estimation sensitivity of an ultrasonic Doppler flow imaging system, comprising:
   (a) ultrasonic wave transmitting and receiving means for sequentially transmitting ultrasonic waves toward and into a living body and for receiving their reflected Doppler-shifted echo signals;
   (b) means for processing a series of echo signals received from each of a number of points within the living body for producing an output signal representative of an estimated flow velocity at each of said points within the body, the processing means including (i) means for detecting the series of echo signals for each point and for calculating an associated power spectrum based on the amplitude-versus-frequency distribution of the series of echo signals, wherein said power spectrum is calculated by maximum entropy means for fitting an Mth order polynomial to the series of echo signals and for detecting therefrom a peak center frequency shift associated with the data detected for each point, and (ii) means for producing an output representative of a velocity estimate from the peak center frequency shift information calculated for each of said points; and
   (c) means for further processing the output signals representative of estimated velocity to produce a two-dimensional color image of the flow being measured.

2. Apparatus according to claim 1 in which the flow being measured is blood flow.

3. Apparatus according to claim 1 including means for removing stationary echo signal components from the echo signals to produce Doppler-shifted components which are then processed in the processing means to produce said velocity estimate.

4. Apparatus according to claim 1 in which the processing means includes means for converting the echo signal into digital data and a corner-turning memory from which the digital data are read prior to removing the stationary echo signal components.

5. Apparatus according to claim 1 in which he processing means includes interpolation network means for calculating the peak frequency shift and segmentation processor means for receiving an estimater maximum average peak frequency value from the interpolation network means to calculate whether the velocity estimate is valid.

6. A system for improving the flow estimation sensitivity of an ultrasonic Doppler flow imaging system, comprising:
   (a) ultrasonic wave transmitting and receiving means for sequentially transmitting ultrasonic waves toward and into a living body and for receiving their reflected Doppler-shifted echo signals;
   (b) means for processing a series of echo signals received from each of a number of points within the living body for producing an output signal representative of an estimated flow velocity at each of said points within the body, the processing means including (i) means for detecting the series of echo signals for each point and for calculating an associated power spectrum based on the amplitude-versus-frequency distribution of the series of echo signals, wherein said power spectrum is calculated by maximum entropy means for fitting a first order polynomial to the series of echo signals and for detecting therefrom a peak center frequency shift associated with the data detected for each point, and (ii) means for producing an output representative of a velocity estimate from the peak center frequency shift information calculated for each of said points; and
   (c) means for further processing the output signals representative of estimated velocity to produce a two-dimensional color image of the flow being measured.

7. Apparatus according to claim 6 in which the processing means produces an output representative of blood flow.

8. Apparatus according to claim 7 including means for removing stationary echo signal components from the echo signals to produce Doppler-shifted components which are then processed in the processing means to produce said velocity estimate.

9. Apparatus according to claim 8 in which the processing means includes means for converting the echo signals to digital data and a corner-turning memory from which the data are read prior to removing the stationary echo components.

10. Apparatus according to claim 6 in which a processing means includes interpolation network means for calculating the peak frequency shift and segmentation processor means for receiving an estimated maximum average peak frequency value from the interpolation network means to calculate whether the velocity estimate is valid.

11. A system for improving the flow estimation sensitivity of an ultrasonic Doppler blood flow imaging system, comprising:
   (a) ultrasonic wave transmitting and receiving means for sequentially transmitting ultrasonic waves toward and into a living body and for receiving their reflected Doppler-shifted echo signals;
   (b) means for processing a series of echo signals received from each of a number of points within the living body for producing an output signal representative of an estimated blood flow velocity at each of said points within the body, the signal processing means including means for detecting the series of echo signals for each point and for calculating an average frequency shift using maximum entropy means of spectral analysis and for producing therefrom an output representative of a velocity estimate from average frequency shift information calculated for each of said points; and
   (c) means for further processing the output signals representative of estimated velocity to produce a two-dimensional color image of the blood flow being measured.

12. Apparatus according to claim 11 in which a power spectrum is calculated by processor means for fitting a first order polynomial to the series of echo signals.

13. Apparatus according to claim 11 in which the processing means includes means for removing stationary echo signal components from the echo signals to produce Doppler-shifted components which are then processed in the processing means to produce said velocity estimate.

14. Apparatus according to claim 13 in which the processing means includes means for converting the echo signals to digital data and a corner-turning memory from which the data are read prior to removing the stationary echo components.

15. Apparatus according to claim 11 in which the processing means includes interpolation network means for calculating the peak frequency shift and segmentation processor means for receiving an estimated maximum average peak frequency value from the interpolation network means to calculate whether the velocity estimate is valid.

16. A system for improving the flow estimation sensitivity of an ultrasonic Doppler blood flow imaging system, comprising:
   (a) ultrasonic wave transmitting and receiving means for sequentially transmitting ultrasonic waves toward and into a living body and for receiving their reflected Doppler-shifted echo signals;
   (b) means for processing a series of echo signals received from each of a number of points within the living body for producing an output signal representative of an estimated blood flow velocity at each of said points within the body, the signal processing means including means for detecting the series of echo signals for each point and for calculating an associated power spectrum based on the amplitude-versus-frequency distribution of the series of echo signals, wherein said calculating means comprises maximum entropy means of processing the series of echo signals to derive the transfer function of a prediction error filter used in the estimation of a maximum average frequency shift for each data point, and means for producing an output representative of a velocity estimate from the average frequency shift information calculated for each of said data points; and
   (c) means for further processing the output signals representative of estimated velocity to produce a two-dimensional color image of the blood flow being measured.

17. Apparatus according to claim 16 including means for removing stationary echo signal components from the echo signals to produce Doppler-shifted components which are then processed in the processing means to produce said velocity estimate.

18. Apparatus according to claim 17 in which the processing means includes means for converting the echo signals to digital data, a corner-turning memory from which the data are read prior to removing the stationary echo components.

19. Apparatus according to claim 16 in which the prediction error filter has an input that is the echo signal series being analyzed and has an output limited to white noise.

20. Apparatus according to claim 16 in which the filter is an all-pole filter and the maximum entropy means are used to calculate one or more coefficients of the filter transfer function.

21. A system for improving the flow estimation sensitivity of an ultrasonic Doppler flow imaging system, comprising:
   (a) ultrasonic wave transmitting and receiving means for sequentially transmitting ultrasonic waves toward and into a living body and for receiving their reflected Doppler-shifted echo signals;
   (b) means for processing a series of echo signals received from each of a number of points within the living body for producing an output signal representative of an estimated flow velocity at each of said points within the body, the processing means including (i) means for detecting the series of echo signals for each point and for calculating an associated power spectrum based on the amplitude-versus-frequency distribution of the series of echo signals, wherein said power spectrum is calculated by means for fitting a first order polynomial to the series of echo signals and for detecting therefrom a peak center frequency shift associated with the data detected for each point, and (ii) means for producing an output representative of a velocity estimate from the peak center frequency shift information calculated for each of said points; and
   (c) means for further processing the output signals representative of estimated velocity to produce a two-dimensional color image of the flow being measured.

* * * * *